US012662689B2

(12) United States Patent
Yoon et al.

(10) Patent No.: US 12,662,689 B2
(45) Date of Patent: Jun. 23, 2026

(54) PROMOTER AND METHOD FOR PRODUCING DESIRED SUBSTANCE USING SAME

(71) Applicant: CJ CHEILJEDANG CORPORATION, Seoul (KR)

(72) Inventors: Byoung Hoon Yoon, Seoul (KR); Jin Sook Chang, Seoul (KR); Seon Hye Kim, Seoul (KR); Ji Hye Lee, Seoul (KR); Sun Hyoung Choi, Seoul (KR); Kyungrim Kim, Seoul (KR); Hyung Joon Kim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 1149 days.

(21) Appl. No.: 17/639,765

(22) PCT Filed: Sep. 1, 2020

(86) PCT No.: PCT/KR2020/011679
§ 371 (c)(1),
(2) Date: Mar. 2, 2022

(87) PCT Pub. No.: WO2021/045472
PCT Pub. Date: Mar. 11, 2021

(65) Prior Publication Data
US 2022/0340940 A1      Oct. 27, 2022

(30) Foreign Application Priority Data
Sep. 2, 2019    (KR) ........................ 10-2019-0108263

(51) Int. Cl.
| | |
|---|---|
| *C12N 1/205* | (2026.01) |
| *C12N 9/04* | (2006.01) |
| *C12N 15/77* | (2006.01) |
| *C12P 13/06* | (2006.01) |
| *C12R 1/15* | (2006.01) |

(52) U.S. Cl.
CPC ............. *C12P 13/06* (2013.01); *C12N 1/205* (2021.05); *C12N 9/0006* (2013.01); *C12N 15/77* (2013.01); *C12Y 101/01086* (2013.01); *C12N 2800/101* (2013.01); *C12R 2001/15* (2021.05)

(58) Field of Classification Search
CPC ...... C12N 1/205; C12N 9/0006; C12N 15/77; C12Y 101/01086
See application file for complete search history.

(56) References Cited

U.S. PATENT DOCUMENTS

| | | | |
|---|---|---|---|
| 8,030,036 | B2 | 10/2011 | Van Dien et al. |
| 8,465,962 | B2 | 6/2013 | Kim et al. |
| 10,113,190 | B2 | 10/2018 | Gerstmeir et al. |
| 10,351,859 | B2 | 7/2019 | Song et al. |
| 2008/0171371 | A1 | 7/2008 | Yukawa et al. |
| 2020/0032305 | A1 | 1/2020 | Lee et al. |

FOREIGN PATENT DOCUMENTS

| | | | |
|---|---|---|---|
| EP | 2 811 028 | A1 | 12/2014 |
| JP | 2015-513892 | A | 5/2015 |
| KR | 10-1335789 | B1 | 12/2013 |
| KR | 10-2016-0015298 | A | 2/2016 |
| KR | 10-2019-0003019 | A | 1/2019 |
| KR | 10-2019-0037224 | A | 4/2019 |
| WO | 2006/028063 | A1 | 3/2006 |

OTHER PUBLICATIONS

Rhee et al., "Transcriptional coupling between the divergent promoters of a prototypic LysR-type regulatory system, the ilvYC operon of *Escherichia coli,*" *PNAS* 96(25):14294-14299 (1999).

GenBank: L09232.1, Corynebacterium glutamicum acetohydroxy acid synthase (ilvB) and (ilvN) genes, and acetohydroxy acid isomeroredeuctase (ilvC) gene, complete cds, 3 pages (Feb. 23, 1995).

GenBank: CP022614.1, Corynebacterium glutamicum ATCC 14067 chromosome, complete genome, 561 pages (Aug. 10, 2017).

Geraskina et al., "Engineering *Escherichia coli* for autoinducible production of L-valine: An example of an artificial positive feedback loop in amino acid biosynthesis," *PLoS One* 14(4):e0215777, 16 pages, (Apr. 25, 2019).

Guo et al., "Generation of Branched-chain Amino Acids Resistant Corynebacterium glutamicum Acetohydroxy Acid Synthase by Site-directed Mutagenesis," *Biotechnology and Bioprocess Engineering* 19:456-467 (2014).

Holátko et al., "Metabolic engineering of the L-valine biosynthesis pathway in *Corynebacterium glutamicum* using promoter activity modulation," *Journal of Biotechnology* 139:203-210 (2009).

Morbach et al., "Engineering the homoserine dehydrogenase and threonine dehydratase control points to analyse flux towards L-isoleucine in *Corynebacterium glutamicum,*" *Appl Microbiol Biotechnol* 45:612-620 (1996).

*Primary Examiner* — Nelson B Moseley, II
*Assistant Examiner* — Dennis J Sullivan
(74) *Attorney, Agent, or Firm* — Seed Intellectual Property Law Group LLP

(57) ABSTRACT

The present application relates to a novel promoter and a method for producing a desired substance using the same.

11 Claims, 2 Drawing Sheets

Specification includes a Sequence Listing.

[FIG. 1]

```
M4           CCGTCTAATTGCATGTGTGTGGTATAAT
M15          CCGTCTAATTGCATGTGTGTGGTATAAT
ATCC14067    CCGTCTAATTGCATGTGTGTGGTAGAAC
ATCC13032    CCGTCTAATTACATGTGTGTGGTAGAAC
ATCC13869    CGGACTAATTACATGTGTGTGGTAGAAC
             *  *  ******  *************  **
```

[FIG. 2]

```
KCCM11201P-ilvC_Pm3_    CCGTCTAATTGCATGTGTGTGGTATAAT
ATCC14067               CCGTCTAATTGCATGTGTGTGGTAGAAC
KCCM11201P              CCGTCTAATTGCATGTGTGTGGTAGAAC
                        **************************  **
```

[FIG. 3]

```
CJ7V-ilvC_Pm3_    CCGTCTAATTGCATGTGTGTGGTATAAT
ATCC14067         CCGTCTAATTGCATGTGTGTGGTAGAAC
CJ7V              CCGTCTAATTGCATGTGTGTGGTAGAAC
                  **************************  **
```

[FIG. 4]

```
CJ8V               CGGACTAATTACATGTGTGTGGTAGAAC
ATCC13869          CGGACTAATTACATGTGTGTGGTAGAAC
CJ8V-ilvC_Pm3_-2   CGGACTAATTACATGTGTGTGGTATAAT
CJ8V-ilvC_Pm3_     CCGTCTAATTGCATGTGTGTGGTATAAT
ATCC14067          CCGTCTAATTGCATGTGTGTGGTAGAAC
                   *  *  ******  *************  **
```

[FIG. 5]

```
KCCM11248P                    CGGACTAATTACATGTGTGTGGTAGAAC
ATCC13869                     CGGACTAATTACATGTGTGTGGTAGAAC
KCCM11248P__ilvC_Pm3_-2       CGGACTAATTACATGTGTGTGGTATAAT
KCCM11248P__ilvC_Pm3_         CCGTCTAATTGCATGTGTGTGGTATAAT
ATCC14067                     CCGTCTAATTGCATGTGTGTGGTAGAAC
                              *  * ****** ************* **
```

[FIG. 6]

```
ATCC13032_hom*lysC*               CCGTCTAATTACATGTGTGTGGTAGAAC
ATCC13032                         CCGTCTAATTACATGTGTGTGGTAGAAC
ATCC13032_hom*lysC*ilvC_Pm3_-3    CCGTCTAATTACATGTGTGTGGTATAAT
ATCC13032_hom*lysC*ilvC_Pm3_      CCGTCTAATTGCATGTGTGTGGTATAAT
ATCC14067                         CCGTCTAATTGCATGTGTGTGGTAGAAC
                                  ********** ************* **
```

[FIG. 7]

```
KCCM11661P-ilvC_Pm3_          CCGTCTAATTGCATGTGTGTGGTATAAT
KCCM11662P-ilvC_Pm3_          CCGTCTAATTGCATGTGTGTGGTATAAT
ATCC14067                     CCGTCTAATTGCATGTGTGTGGTAGAAC
KCCM11661P                    CCGTCTAATTGCATGTGTGTGGTAGAAC
KCCM11662P                    CCGTCTAATTGCATGTGTGTGGTAGAAC
                              ************************* **
```

[FIG. 8]

```
CJL8001                       CCGTCTAATTACATGTGTGTGGTAGAAC
ATCC13032                     CCGTCTAATTACATGTGTGTGGTAGAAC
CJL8001-ilvC_Pm3_-3           CCGTCTAATTACATGTGTGTGGTATAAT
CJL8001-ilvC_Pm3_             CCGTCTAATTGCATGTGTGTGGTATAAT
ATCC14067                     CCGTCTAATTGCATGTGTGTGGTAGAAC
                              ********** ************* **
```

PROMOTER AND METHOD FOR PRODUCING DESIRED SUBSTANCE USING SAME

The Sequence Listing associated with this application is provided in text format in lieu of a paper copy, and is hereby incorporated by reference into the specification. The name of the text file containing the Sequence Listing is 200187_482USPC_SEQUENCE LISTING.txt. The text file is 8,067 bytes, was created on Feb. 28, 2022, and is being submitted electronically via EFS-Web.

TECHNICAL FIELD

The present disclosure relates to a novel promoter and a method for producing a target substance using the same.

BACKGROUND ART

Coryneform microorganisms are industrial microorganisms that have been most widely and traditionally used to produce amino acids and nucleic acid-related substances. Coryneform microorganisms are gram-positive bacteria that are mainly used to produce chemical substances having various applications in the fields of animal feed, drugs, medicines, foods, and the like, including amino acids and various kinds of nucleic acids, and require biotin for growth thereof. These bacteria are characterized by bending at the right angle during cell division (snapping), and one of the advantages thereof is that they have low degradation activity for the metabolites produced.

Among products produced by coryneform microorganisms, L-amino acids are basic structural units of a protein, and are used as an important material for pharmaceutical raw materials, food additives, animal feeds, nutritional supplements, pesticides, disinfectants, and the like. Therefore, the industrial production of amino acids has become an economically important industrial process.

Various studies have been conducted for efficient production of amino acids; for example, efforts have been made to develop microorganisms or fermentation process technologies for production of amino acids with high efficiency. Specifically, methods of approach specific to target substances have been developed, such as increasing the expression of genes encoding enzymes involved in the biosynthesis of amino acids or deleting genes unnecessary for the biosynthesis of amino acids in strains of the genus *Corynebacterium* (U.S. Pat. No. 8,030,036 B2, etc.). In addition to these methods, a method for removing genes that are not involved in the production of amino acids and a method for removing genes whose functions for producing amino acids are not specifically known have also been utilized. However, there is still a growing need to study methods for efficient production of amino acids with high yield.

To develop high-titer strains from such coryneform microorganisms by genetic engineering or metabolic engineering, the expression of genes involved in several metabolic pathways in the microorganisms should be selectively regulated. For such regulation, it is important to regulate the activity of a promoter, which is a regulatory gene, at which the transcription initiates by binding of RNA polymerase to the DNA molecule.

DISCLOSURE

Technical Problem

The present inventors have made efforts to develop a promoter exhibiting a strong expression inducing activity, and as a result, the present inventors have modified the ilvC gene promoter on the *Corynebacterium* chromosome through nucleotide substitution and identified that the modified promoter can increase the expression of a gene operably linked thereto, thereby completing the present disclosure.

Technical Solution

The present disclosure provides a polynucleotide having a promoter activity, in which at least one nucleotide is substituted with another nucleotide in the nucleotide sequence of SEQ ID NO: 1.

The present disclosure provides a promoter including the polynucleotide.

The present disclosure provides a vector including the promoter and a gene encoding a target protein.

The present disclosure provides a microorganism of the genus *Corynebacterium,* including the polynucleotide.

The present disclosure provides a method for producing a target substance, the method including culturing the microorganism of the genus *Corynebacterium* in a medium.

The present disclosure provides a method for enhancing the expression of a target gene, the method including operably linking the promoter to the target gene.

The present disclosure provides use, as a promoter, of a polynucleotide in which at least one nucleotide is substituted with another nucleotide in the nucleotide sequence of SEQ ID NO: 1.

Advantageous Effects

The polynucleotides having activity of novel promoters of the present disclosure can be used to increase the expression of a target gene linked thereto, and thus can be helpfully used in the production of target substances.

BRIEF DESCRIPTION OF DRAWINGS

FIGS. 1 to 4 show ilvC promoter regions of valine-producing strains.

FIGS. 5 and 6 show ilvC promoter regions of isoleucine-producing strains.

FIGS. 7 and 8 show ilvC promoter regions of leucine-producing strains.

DETAILED DESCRIPTION OF THE INVENTION

Hereinafter, the present disclosure will be described in detail. Each description and embodiment of an aspect disclosed herein may be applied to a description and embodiment of another aspect with respect to overlapping contents. In addition, all combinations of various elements disclosed in the detailed description of the present disclosure belong to the scope of the present disclosure. Furthermore, the scope of the present disclosure should not be limited by the specific description provided below.

Further, those skilled in the art will recognize, or be able to ascertain, by using no more than routine experimentation, many equivalents to the specific embodiments of the disclosure described herein. Such equivalents are intended to be encompassed by the present disclosure.

According to an aspect of the present disclosure, there is provided a polynucleotide in which at least one nucleotide is substituted with another nucleotide in the nucleotide sequence of SEQ ID NO: 1 and which has a promoter activity.

As used herein, the term "polynucleotide" refers to a nucleotide polymer composed of nucleotide monomers covalently linked in a long chain, such as a DNA strand having a predetermined length or longer.

As used herein, the term "polynucleotide having a promoter activity" refers to a DNA region present in the vicinity of a site, which is involved in the transcription of a target gene, including a site to which RNA polymerase, an enhancer, or the like binds, for the expression of the target gene to be linked downstream thereof. For the purposes of the present disclosure, the polynucleotide may be used as an enhanced promoter for general use. The polynucleotide may be one configured to regulate the expression of a target gene operably linked thereto and the production and/or activity of a protein encoded by the target gene and may be one configured to increase the production and/or activity of a target product (a biologically active substance, e.g., at least one selected from the group consisting of amino acids, nucleic acids, vitamins, proteins, fatty acids, and organic acids), of which the production involves the protein, in cells, compared with conventional promoters or cell endogenous promoters, but is not limited thereto.

In an embodiment, the polynucleotide having a promoter activity of the present disclosure may be used as a promoter capable of enhancing the expression of acetohydroxy acid isomeroreductase. The polynucleotide may be a polynucleotide involved in increasing the production or production amount of amino acids including amino acids, specifically branched-chain amino acids, more specifically leucine, valine, and isoleucine, but is not limited thereto, and polynucleotide sequences having a promoter activity are included without limitation.

In the present disclosure, SEQ ID NO: 1 is a sequence having a promoter activity, and the nucleotide sequence of SEQ ID NO: 1 can be identified from the known database NCBI Genbank, and may be derived from *Corynebacterium* sp., but is not limited thereto. Any sequence that has the same activity as the nucleotide sequence may be included without limitation. Meanwhile, SEQ ID NO: 1 may be a promoter of acetohydroxy acid isomeroreductase. However, the sequence is not limited thereto.

As used herein, the term "acetohydroxy acid isomeroreductase" refers to an enzyme involved in the biosynthesis of an L-branched-chain amino acid. As for the biosynthesis pathway of L-branched-chain amino acids, first, acetohydroxy acid synthase catalyzes the decarboxylation of pyruvic acid and the condensation reaction of the pyruvic acid with another pyruvic acid molecule to produce acetolactic acid, a precursor of valine, or the decarboxylation of pyruvic acid and the condensation reaction of the pyruvic acid with 2-ketobutyrate to produce acetohydroxybutyrate, a precursor of isoleucine. Acetohydroxy acid isomeroreductase advances the reaction to the next step by using the acetolactic acid or acetohydroxybutyrate thus produced as a substrate, thereby producing L-valine, L-leucine, and L-isoleucine. Specifically, isomerization occurs by the reaction of acetolactic acid or acetohydroxybutyrate, produced by the reaction of acetohydroxy acid synthase, with acetohydroxy acid isomeroreductase, and then through a reduction reaction, (2R)-2,3-dihydroxy-3-isovalerate or (2R3R)-2,3-dihydroxy-3-methylvalerate is produced from each substrate. (2R)-2,3-Dihydroxy-3-isovalerate is subjected to the reactions catalyzed by dihydroxy acid dehydratase and transaminase B to produce L-valine, and sequentially subjected to the reactions catalyzed by dihydroxy acid dehydratase, 2-isopropylmalate synthase, isopropylmalateisomerase, 3-isopropylmalate dehydrogenase, and transaminase B to produce L-leucine. (2R,3R)-2,3-Dihydroxy-3-methylvalerate is subjected to the reactions catalyzed by dihydroxy acid dehydratase and transaminase B to produce L-isoleucine. Therefore, acetohydroxy acid isomeroreductase is an important enzyme in the biosynthesis pathway of an L-branched-chain amino acid.

The polynucleotide having a promoter activity of the present disclosure refers to one in which at least one nucleotide is substituted with another nucleotide in the nucleotide sequence of SEQ ID NO: 1 and/or a nucleotide sequence having at least 70%, 80%, 85%, 90%, 95%, 96%, 97%, 98%, or 99% homology or identity with SEQ ID NO: 1. The nucleotide sequences having homology or identity may be those within the above range excluding the sequence having 100% identity, or may be sequences having less than 100% identity.

Specifically, the polynucleotide having a promoter activity may include a polynucleotide having a promoter activity in which at least one nucleotide is substituted with another nucleotide in the nucleotide sequence of SEQ ID NO: 1, or may be composed of a polynucleotide having a promoter activity in which at least one nucleotide is substituted with another nucleotide in the nucleotide sequence of SEQ ID NO: 1.

The polynucleotide having a promoter activity may be a polynucleotide represented by the general formula X-Y-Z wherein i) X is CNGN; ii) Y is CTAATTN; and iii) Z is CATGTGTGTGGTANAAN; and iv) N is selected from adenine (A), thymine (T), guanine (G), or cytosine (C). In the polynucleotide sequence of the general formula, Z may be composed of SEQ ID NO: 2, Y may be composed of SEQ ID NO: 3, or X may be composed of SEQ ID NO: 4.

Specifically, in the general formula, X may be represented by $CN_1GN_2$, Y may be represented by $CTAATTN_3$, and Z may be represented by CATGTGTGTGGTATAAT, in which $N_1$, $N_2$, and $N_3$ each are any one selected from adenine (A), thymine (T), guanine (G), or cytosine (C).

More specifically, in the general formula, i) $N_1$ may be cytosine (C) or guanine (G), ii) $N_2$ may be adenine (A) or thymine (T), iii) N3 may be adenine (A) or guanine (G), or iv) there may be a combination of substitutions of i) to iii), but is not limited thereto.

In an embodiment, in the polynucleotide sequence of the general formula, in Z, the 14th nucleotide N and the 17th nucleotide may be thymine (T) in the nucleotide sequence set forth in SEQ ID NO: 2, wherein in X, the 2nd nucleotide N may be cytosine (C) or guanine (G) and the 4th nucleotide N may be adenine (A) or thymine (T) in the nucleotide sequence set forth in SEQ ID NO: 4 or X may be any one of SEQ ID NOS: 8 to 11; and in Y, the 7th nucleotide N may be adenine (A) or guanine (G) in the nucleotide sequence set forth in SEQ ID NO: 3. Specifically, in Z, the 14th nucleotide N and the 17th nucleotide may be thymine (T) in the nucleotide sequence set forth in SEQ ID NO: 2; X may be any one of SEQ ID NOS: 8 to 11; and Y may be SEQ ID NO: 6 or 7.

In still another embodiment, the polynucleotide may have any one polynucleotide sequence selected from SEQ ID NOS: 13 to 20.

Although described using the expression "polynucleotide having a nucleotide sequence set forth in a particular sequence number" or "polynucleotide including a nucleotide sequence set forth in a particular sequence number" in the present disclosure, it would be obvious that a polynucleotide having a polynucleotide sequence having a deletion, a modification, a substitution, or an addition in a part thereof may also be used in the present disclosure, as long as the polynucleotide has an activity identical or corresponding to that of the polypeptide consisting of the nucleotide sequence of the corresponding sequence number. For example, it would be obvious that such expressions do not exclude any addition of nonsense sequences upstream or downstream of the nucleotide sequence of the corresponding sequence number, a naturally occurring mutation, or a silent mutation thereof, as long as the polynucleotide has activity identical or equivalent to that of the polynucleotide, and nucleotide sequences having such a sequence addition or mutation are also within the scope of the present disclosure.

The homology or identity refers to a degree of relatedness between two given nucleotide sequences and may be expressed as a percentage.

The terms homology and identity may often be used interchangeably.

The sequence homology or identity of conserved polynucleotides may be determined by a standard alignment algorithm, and default gap penalties established by a program to be used may be used together. Substantially, homologous or identical sequences may generally hybridize with each other along the entire sequences or at least about 50%, 60%, 70%, 80%, or 90% of the full lengths of the sequences under moderate or highly stringent conditions. In the polynucleotides to be hybridized, a polynucleotide containing a degenerate codon instead of a codon is also considered.

Whether any two polynucleotide sequences have homology, similarity, or identity may be determined using a known computer algorithm, such as the "FASTA" program, by using default parameters as in Pearson et al. (1988) *Proc. Natl. Acad. Sci. USA* 85:2444. Alternatively, this may be determined using the Needleman-Wunsch algorithm (Needleman and Wunsch, 1970, *J. Mol. Biol.* 48:443-453), which is performed in the Needleman program of the European Molecular Biology Open Software Suite (EMBOSS) package (Rice et al., 2000, *Trends Genet.* 16:276-277) (version 5.0.0 or versions thereafter) (GCG program package (including GCG program package (Devereux, J., et al., *Nucleic Acids Research* 12:387 (1984)), BLASTP, BLASTN, FASTA (Atschul, S. F., et al., *J MOLEC BIOL* 215:403 (1990); *Guide to Huge Computers,* Martin J. Bishop, ed., Academic Press, San Diego,1994, and CARILLO et al. (1988) *SIAM J Applied Math* 48:1073). For example, the homology, similarity, or identity may be determined using BLAST from the National Center for Biotechnology Information database, or ClustalW.

The homology, similarity, or identity of polynucleotides may be determined by comparing sequence information through the GAP computer program, for example, Needleman et al., (1970), *J Mol Biol.* 48:443, as disclosed in Smith and Waterman, *Adv. Appl. Math* (1981) 2:482. Briefly, the GAP program defines the homology, similarity, or identity as the value obtained by dividing the number of similarly aligned symbols (i.e., nucleotides or amino acids) by the total number of the symbols in the shorter of the two sequences. The default parameters for the GAP program may include: (1) a binary comparison matrix (containing a value 1 for identity and a value 0 for non-identity) and the weighted comparison matrix of Gribskov et al. (1986) *Nucl. Acids Res.* 14:6745 as disclosed in Schwartz and Dayhoff, eds., *Atlas Of Protein Sequence And Structure,* National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or a gap open penalty of 10 and a gap extension penalty of 0.5); and

6

(3) no penalty for end gaps. Therefore, the term "homology" or "identity" used herein refers to the relatedness between sequences.

In addition, any polynucleotide sequence that can hybridize with a probe capable of being prepared from a known gene, for example, a sequence complementary to a part or the entirety of the above-described polynucleotide sequence, under stringent conditions and which has the same activity may be included without limitation. The term "stringent conditions" refers to conditions that enable specific hybridization between polynucleotides. Such conditions are specifically disclosed in the literature (e.g., J Sambrook et al., supra). For example, the conditions may include conditions under which genes having high homology or identity, such as genes having at least 40%, specifically at least 70%, at least 80%, at least 85%, or at least 90%, more specifically at least 95%, still more specifically at least 97%, and even still more specifically at least 99% homology or identity hybridize with each other, but genes having lower homology or identity than the above ranges do not hybridize with each other; or typical washing conditions for Southern hybridization, i.e., washing is conducted once, specifically twice or three times at a salt concentration and temperature corresponding to 60° C., 1×SSC, and 0.1° A SDS, specifically 60° C., 0.1×SSC, and 0.1% SDS, and more specifically 68° C., 0.1×SSC, and 0.1% SDS.

Hybridization requires that two nucleic acids have complementary sequences, although mismatches between bases may be possible depending on hybridization stringency. The term "complementary" is used to describe the relationship between nucleotide bases that can hybridize with each other. For example, in DNA, adenine is complementary to thymine and cytosine is complementary to guanine. Therefore, the present disclosure may include not only substantially similar nucleic acid sequences but also isolated nucleic acid fragments complementary to the entire sequence.

Specifically, polynucleotides having homology or identity can be detected at a $T_m$ value of 55° C. by using hybridization conditions that include a hybridization step and using the above-described conditions. In addition, the $T_m$ value may be 60° C., 63° C., or 65° C., but is not limited thereto, and may be appropriately controlled by a person skilled in the art according to the purpose.

The appropriate stringency for hybridizing polynucleotides depends on the length of the polynucleotides and the degree of complementarity thereof, and variables thereof are well known in the art (see Sambrook et al., supra, 9.50-9.51, 11.7-11.8).

According to another aspect of the present disclosure, there is provided a promoter including the polynucleotide of the present disclosure.

As used herein, the term "promoter" refers to an untranslated nucleotide sequence, which is located upstream of the coding region, contains a binding site for RNA polymerase, and has activity to initiate the transcription of a target gene into mRNA, that is, a DNA region to which RNA polymerase binds to thereby initiate the transcription of the gene. The promoter may be located at the 5'-region of the initiation site of the transcription into mRNA.

The promoter of the present disclosure may have a promoter activity that is enhanced compared with conventional promoters. That is, the promoter can increase the expression of a target gene as well as the expression and activity of a protein encoded by the target gene.

For the purposes of the present disclosure, the target gene for expression enhancement may be appropriately changed depending on a product to be produced, that is, a "target product", and the promoter may be used as a general-purpose promoter for enhancement of the target gene.

The term "target gene", for the purposes of the present disclosure, refers to a gene whose expression is regulated by the promoter sequence of the present disclosure. The protein encoded by the target gene may be expressed as a "target protein", and the gene encoding the "target protein" may be expressed as a "target gene". For example, the target gene of the promoter may be a gene encoding acetohydroxy acid isomeroreductase, that is, it may be ilvC, but is not limited thereto.

The polynucleotide encoding the target protein may have various modifications in the coding region thereof within the scope in which the polynucleotide sequence is not changed, due to codon degeneracy or in consideration of the codons preferred by an organism in which the polynucleotide is to be expressed. A description of the polynucleotide sequence is as described above.

According to still another aspect of the present disclosure, there is provided a vector including the promoter of the present disclosure.

According to still another aspect of the present disclosure, there is provided a vector including the promoter of the present disclosure and a gene encoding a target protein.

Specifically, the vector may be a vector wherein the target protein is acetohydroxy acid isomeroreductase, but is not limited thereto.

As used herein, the term "vector" refers to a DNA construct containing a nucleotide sequence encoding a target polynucleotide, which is operably linked to an appropriate expression control region or an expression control sequence so as to express the target polynucleotide in an appropriate host. The expression control sequence may include a promoter capable of initiating transcription, any operator sequence for controlling such transcription, a sequence for encoding an appropriate mRNA ribosomal binding site, and sequences for controlling the termination of transcription and translation, and specifically, the expression control sequence may include the promoter of the present disclosure. The vector, after transformation into an appropriate host, can replicate or function independently of the genome of the host, or may be integrated into the genome itself.

For example, the replacement with a target polynucleotide in a chromosome may be achieved through a vector for chromosomal insertion in a cell. The insertion of the polynucleotide into the chromosome may be performed using any method known in the art, for example, homologous recombination, but is not limited thereto. The vector may further include a selection marker for identifying the insertion of the chromosome. A selection marker is used for selection of cells transformed with the vector, that is, to confirm whether the target nucleotide molecule has been successfully inserted, and markers for imparting selectable phenotypes, such as drug resistance, auxotrophy, resistance to cytotoxic drugs, and expression of surface proteins, may be used. Under the circumstances where selective agents are treated, only the cells capable of expressing the selection markers can survive or express other phenotypic traits, so that the transformed cells can be selected.

The vector used in the present application is not particularly limited, and any vector known in the art may be used. Examples of the vector commonly used may include native or recombinant plasmids, cosmids, viruses, and bacteriophages. For example, pWE15, M13, MBL3, MBL4, IXII, ASHII, APII, t10, t11, Charon4A, Charon21A, and the like may be used as phage vectors or cosmid vectors, and pBR-based, pUC-based, pBluescriptII-based, pGEM-based, pTZ-based, pCL-based, and pET-based vectors may be used as plasmid vectors. Specifically, pDZ, pACYC177, pACYC184, pCL, pECCG117, pUC19, pBR322, pMW118, pCC1BAC, or the like may be used.

According to still another aspect of the present disclosure, there is provided a *Corynebacterium* sp. microorganism containing the polynucleotide having a promoter activity of the present disclosure.

According to still another aspect of the present disclosure, there is provided a *Corynebacterium* sp. microorganism containing the polynucleotide of the present disclosure and a gene encoding the target protein.

As used herein, the term "microorganism" encompasses all wild-type microorganisms, or microorganisms with a naturally or artificially genetic modification, and refers to a microorganism in which a particular mechanism is attenuated or enhanced due to the insertion of an exogenous gene or the enhancement or attenuation of activity of an endogenous gene. The microorganism of the present disclosure may include a microorganism into which the polynucleotide having a promoter activity of the present disclosure is introduced or which includes the polynucleotide, without limitation.

Specifically, the microorganism is a microorganism prepared by transformation with a vector containing the polynucleotide having a promoter activity of the present disclosure and a gene encoding a target protein, or a microorganism including the polynucleotide having a promoter activity and a gene encoding a target protein or including a vector containing these. Specifically, the microorganism may be a microorganism including the polynucleotide having a promoter activity and a gene encoding a target protein, and thus has the ability to produce the target protein or a target product, of which the production involves the target protein, but is not limited thereto. The microorganism may be a microorganism naturally having the ability to produce a target protein or a target product, or a microorganism obtained by imparting the ability to produce a target protein or a target product to a parent strain without the ability to produce a target protein or a target product, but is not limited thereto.

As used herein, the term "microorganism producing a target protein or a target product" encompasses all of wild-type microorganisms or microorganisms with a naturally or artificially occurring genetic modification, and refers to a microorganism in which a particular mechanism is attenuated or enhanced due to the insertion of an exogenous gene or the enhancement or inactivation of activity of an endogenous gene, wherein the microorganism may have a genetic mutation for the production of a target protein or product. The corresponding microorganism may be: a microorganism genetically modified through any one of a target protein, a polynucleotide encoding the same, and a vector including the polynucleotide; a microorganism modified to express the protein or a polynucleotide encoding the same; a recombinant microorganism expressing the target protein or a polynucleotide encoding the same; or a recombinant microorganism having the activity of the target protein, but is not limited thereto.

As used herein, the term "transformation" indicates that a polynucleotide or vector containing the polynucleotide of the present disclosure and a polynucleotide encoding a target protein is introduced into a host cell or a microorganism to allow the target protein to be expressed in the host cell. Any host cell may be included as long as the target protein can be expressed in the host cell, regardless of whether the polynucleotide or vector inserted in the host cell or microorganism is inserted and located in the chromosome of the host cell or located outside of the chromosome. The polynucleotide can be introduced in any form as long as the polynucleotide can be introduced and expressed in the host cell. For example, the polynucleotide may be introduced, in the host cell, in the form of an expression cassette, which is a gene construct containing all factors required for self-expression. The expression cassette may usually include a promoter operably linked to the polynucleotide, a transcription termination signal, a ribosome binding site, and a translation terminal signal, and the promoter may be a polynucleotide having a promoter activity of the present disclosure. The expression cassette may be an expression vector enabling self-replication. In addition, the polynucleotide encoding the target protein may be operably linked to the polynucleotide of the present disclosure and introduced as-is in the host cell, but is not limited thereto.

As used herein, the term "operably linked" refers to a functional linkage between a gene sequence and a promoter sequence which initiates and mediates the transcription of the polynucleotide encoding the target protein. The promoter sequence may be the promoter provided in the present disclosure.

A method for transformation with the vector of the present disclosure includes any method of introducing a nucleic acid into a cell, and any suitable standard technique known in the art may be selected and performed depending on the host cell. Examples of the technique may be electroporation, calcium phosphate ($CaPO_4$) precipitation, calcium chloride ($CaCl_2$) precipitation, microinjection, a polyethyleneglycol (PEG) method, a DEAE-dextran method, a cationic liposome method, a lithium acetate-DMSO method, and the like, but are not limited thereto.

For the purposes of the present disclosure, the microorganism is a microorganism producing a target protein or a target product, wherein the microorganism has an increased ability to produce a target protein or a target product by including the polynucleotide of the present disclosure.

In an embodiment, the microorganism including the polynucleotide of the present disclosure may be a microorganism which has an enhanced activity of a target protein due to a substitution of at least one nucleotide with another nucleotide in the polynucleotide sequence of SEQ ID NO: 1, but is not limited thereto.

Specifically, the microorganism is a microorganism including a polynucleotide which has a promoter activity due to a substitution of at least one nucleotide with another nucleotide in the polynucleotide sequence of SEQ ID NO: 1, wherein the polynucleotide having a promoter activity may be represented by the general formula X-Y-Z, in which X is CNGN; Y is CTAATTN; and Z is CATGTGTGTGGTA-NAAN; and N is selected from adenine (A), thymine (T), guanine (G), or cytosine (C). The polynucleotide is as described above.

In an embodiment, the microorganism of the present disclosure may have an enhanced activity of a target protein due to transformation with a vector including the polynucleotide of the present disclosure and a gene encoding the target protein.

In the present disclosure, the microorganism producing a target protein or a target product or the microorganism having the ability to produce a target protein or a target product may be a microorganism in which some of the genes involved in the biosynthesis pathway of the target protein or product are enhanced or attenuated, or some of the genes involved in the degradation pathway of the target protein or target product are enhanced or attenuated.

For example, when the target protein is a protein involved in the production of a branched-chain amino acid, the microorganism may be a microorganism naturally having the ability to produce the branched-chain amino acid or a microorganism obtained by imparting the ability to produce a branched-chain amino acid to a parent strain without the ability to produce a branched-chain amino acid, but is not limited thereto.

In an embodiment, when the target protein is acetohydroxy acid isomeroreductase, the microorganism may be a cell or a microorganism in which the polynucleotide of the present disclosure is operably linked to a gene encoding acetohydroxy acid isomeroreductase to enhance the activity of acetohydroxy acid isomeroreductase, and in such cases, the host cell or microorganism may be a microorganism capable of producing a branched-chain amino acid via the target protein.

Herein, the "microorganism capable of producing a branched-chain amino acid" may be used interchangeably with the "microorganism producing a branched-chain amino acid" and "microorganism having the ability to produce a branched-chain amino acid".

As used herein, the term "branched-acid amino acid" refers to an amino acid with a branched alkyl group on the side chain thereof, which includes valine, leucine, and isoleucine. Specifically, in the present disclosure, the branched-chain amino acid may be an L-branched-chain amino acid, and the L-branched-chain amino acid may be L-valine, L-isoleucine, or L-leucine, but is not limited thereto.

As used herein, the term "microorganism producing a branched-chain amino acid" encompasses all wild-type microorganisms or microorganisms with a naturally or artificially occurring genetic modification, and refers to a microorganism in which a particular mechanism is attenuated or enhanced due to the insertion of an exogenous gene or the enhancement or inactivation of activity of an endogenous gene, wherein the microorganism may have a genetic mutation or an enhanced activity for the production of a target branched-chain amino acid. For the purposes of the present disclosure, the microorganism producing a branched-chain amino acid may be a microorganism which has an increased ability to produce a target branched-chain amino acid by including the polynucleotide having a promoter activity of the present disclosure, and specifically, the microorganism may be a microorganism of the genus *Corynebacterium*. Specifically, the microorganism producing a branched-chain amino acid or the microorganism having the ability to produce a branched-chain amino acid may be a microorganism in which some of the genes involved in the biosynthesis pathway of the branched-chain amino acid are enhanced or attenuated, or some of the genes involved in the degradation pathway of the branched-chain amino acid are enhanced or attenuated. For example, the microorganism producing a branched-chain amino acid may have an increased expression of ilvC encoding acetohydroxy acid isomeroreductase due to inclusion of the polynucleotide having a promoter activity provided in the present disclosure, but is not limited thereto.

As used herein, the term "microorganism of the genus *Corynebacterium* producing a branched-chain amino acid" may be a microorganism of the genus *Corynebacterium* having the ability to produce a branched-chain amino acid in nature or through a modification. Specifically, the microorganism of the genus *Corynebacterium* producing a branched-chain amino acid of the present disclosure may be a microorganism of the genus *Corynebacterium* which includes ilvC encoding acetohydroxy acid isomeroreductase and has enhanced ability to produce a branched-chain amino acid through the enhancement of the promoter activity of ilvC. More specifically, the microorganism of the genus *Corynebacterium* producing a branched-chain amino acid of the present disclosure may be a microorganism of the genus *Corynebacterium* which includes the polynucleotide having a promoter activity of the present disclosure or has an increased ability to produce a branched-chain amino acid due to transformation with a vector containing the polynucleotide and a gene encoding the target protein.

The "microorganism of the genus *Corynebacterium* having the ability to produce a branched-chain amino acid" refers to a microorganism having an increased ability to produce a branched-chain amino acid compared with a parent strain before transformation or an unmodified microorganism. The "unmodified microorganism" refers to a wild-type strain itself, a microorganism not including a gene encoding acetohydroxy acid isomeroreductase, or a microorganism not including the polynucleotide sequence of the present disclosure or not transformed with a vector containing the polynucleotide of the present disclosure and a gene encoding a target protein.

The "parent strain" may be a microorganism of the genus *Corynebacterium* producing a branched-chain amino acid. Specifically, the parent strain may be a microorganism producing a branched-chain amino acid with a naturally or artificially occurring genetic modification. For example, the parent strain may be a strain having an improved ability to produce L-valine due to the introduction of a modification (ilvN(A42V); *Biotechnology and Bioprocess Engineering*, June 2014, Volume 19, Issue 3, pp. 456-467) into a microorganism of the genus *Corynebacterium*, or a strain having an improved ability to produce L-isoleucine due to the introduction of a lysC(L377K) variant and a hom(G378E) variant (*Appl. Microbiol. Biotechnol*. 45, 612-620 (1996)) into a microorganism of the genus *Corynebacterium* and the introduction of an ilvA(V383A) modification (*World J Microbiol Biotechnol* (2015) 31:1369-1377) into a gene encoding L-threonine dehydratase. In addition, the parent strain may be a strain having an improved ability to produce L-leucine due to the introduction of a modification (leuA (R558H, G561D); US 2020-0032305 A1) into a microorganism of the genus *Corynebacterium*, but is not limited thereto.

In the present disclosure, the "microorganism of the genus *Corynebacterium*" may include all the microorganisms of the genus *Corynebacterium*. Specifically, examples thereof may be *Corynebacterium glutamicum, Corynebacterium ammoniagenes, Brevibacterium lactofermentum, Brevibacterium flavum, Corynebacterium thermoaminogenes, Corynebacterium efficiens, Corynebacterium stationis, Corynebacterium crudilactis, Corynebacterium deserti, Corynebacterium callunae, Corynebacterium singulare, Corynebacterium halotolerans, Corynebacterium striatum, Corynebacterium pollutisoli, Corynebacterium imitans, Corynebacterium testudinoris, Corynebacterium flavescens*, and the like, but are not limited thereto.

According to still another aspect of the present disclosure, there is provided a method for producing a target substance, the method including culturing the microorganism of the genus *Corynebacterium* in a medium.

The target substance may specifically be an amino acid, and more specifically a branched-chain amino acid, but is not limited thereto.

In the method, the culturing of the microorganism may be performed by known bath culturing, continuous culturing, fed-batch culturing, or the like, but is not limited thereto. The culture conditions may not be particularly limited, but the adjustment to appropriate pH (e.g., pH 5 to pH 9, specifically pH 6 to pH 8, and most specifically pH 6.8) may be achieved using a basic compound (e.g., sodium hydroxide, potassium hydroxide, or ammonia) or an acidic compound (e.g., phosphoric acid or sulfuric acid), and an aerobic condition may be maintained by adding oxygen or oxygen-containing gas mixture to the culture. The culturing temperature may be maintained at 20° C. to 45° C., and specifically at 25° C. to 40° C., and the culturing may be performed for about 10 to 160 hours, but the conditions are not limited thereto. The amino acid produced by the culturing may be released into the medium or may remain in cells without being released.

In the medium for culturing to be used, as a carbon source, sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palm itic acid, stearic acid, and linoleic acid), alcohols (e.g., glycerol and ethanol), organic acids (e.g., acetic acid), and the like may be used alone or in combination, but the carbon source is not limited thereto. As a nitrogen source, a nitrogen-containing organic compound (e.g., a peptone, a yeast extract, a meat extract, a malt extract, corn steep liquor, a soybean flour, and urea) or an inorganic compound (e.g., ammonium sulfate, ammonium chloride, ammonium phosphate, ammonium carbonate, and ammonium nitrate), and the like may be used alone or in combination, but the nitrogen source is not limited thereto. As a phosphorus source, potassium dihydrogen phosphate, dipotassium hydrogen phosphate, a sodium-containing salt corresponding thereto, and the like may be used alone or in combination, but the phosphorus source is not limited thereto. In addition, the medium may contain essential growth-promoting materials, such as other metal salts (e.g., magnesium sulfate or iron sulfate), amino acids, and vitamins.

The method for producing a target substance of the present disclosure may further include recovering the target substance from the medium.

For recovering the target substance produced in the culturing step, the target substance may be collected from the medium by using an appropriate method known in the art according to the culturing method. For example, centrifugation, filtration, anion-exchange chromatography, crystallization, HPLC, and the like may be used, and the target substance can be recovered from the medium or microorganism by using an appropriate method known in the art.

In addition, the recovering step may include a purification process, which may be performed using an appropriate method known in the art. For example, when the target substance is an amino acid, the recovered amino acid may have a purified form or may be a microorganism fermentation broth containing an amino acid (*Introduction to Biotechnology and Genetic Engineering*, A. J. Nair., 2008).

According to another aspect of the present disclosure, there is provided a method for enhancing the expression of a target gene, the method including operably linking a promoter including the polynucleotide of the present disclosure to the target gene.

The polynucleotide, target gene, promoter, and the like are as described above.

According to another aspect of the present disclosure, there is provided use, as a promoter, of a polynucleotide having a substitution of at least one nucleotide with another nucleotide in the nucleotide sequence of SEQ ID NO: 1.

The polynucleotide is as described above.

MODE FOR CARRYING OUT THE INVENTION

Hereinafter, the present disclosure will be described in detail with reference to exemplary embodiments. However, these exemplary embodiments are provided for specifically illustrating the present disclosure, and the scope of the present disclosure is not limited thereto.

EXAMPLE 1

Selection of Mutant Strain with Increased Valine Producing Ability Through Random Mutation

Example 1-1: Random Mutagenesis Through UV Irradiation

In order to select mutant strains with increased valine producing ability, *Corynebacterium glutamicum* KCCM11201P (U.S. Pat. No. 8,465,962 B2), which is a valine-producing strain, was plated on nutrient media containing agar and cultured at 30° C. for 36 hours. The hundreds of colonies thus obtained were irradiated with UV at room temperature to perform random mutagenesis on the genome in the strain.

<Nutrient Medium (pH 7.2)> glucose 10 g, meat juice 5 g, polypeptone 10 g, sodium chloride 2.5 g, yeast extract 5 g, agar 20 g, and urea 2 g (based on 1 L of distilled water).

Example 1-2

Fermentation Titer Test on Mutagenized Strains and Selection of Strains

In order to select mutant strains with an increased L-valine producing ability compared with *Corynebacterium glutamicum* KCCM11201P used as a parent strain, a fermentation titer test was performed on the mutagenized strains. Each colony was subcultured in nutrient media, and then each strain was inoculated into a 250 mL corner-baffle flask containing 25 mL of a production medium, and cultured with shaking at 30° C. at 200 rpm for 72 hours. Thereafter, the concentration of L-valine was analyzed using HPLC, and the analyzed concentrations of L-valine were tabulated in Table 1.

<Nutrient Medium (pH 7.2)> glucose 10 g, meat juice 5 g, polypeptone 10 g, sodium chloride 2.5 g, yeast extract 5 g, agar 20 g, and urea 2 g (based on 1 L of distilled water).

<Production Medium (pH 7.0)> glucose 100 g, ammonium sulfate 40 g, soy protein 2.5 g, corn steep solids 5 g, urea 3 g, potassium phosphate dibasic 1 g, magnesium sulfate heptahydrate 0.5 g, biotin 100 μg, thiamine-HCl 1 mg, calcium pantothenate 2 mg, nicotine amide 3 mg, calcium carbonate 30 g (based on 1 L of distilled water)

TABLE 1

| | Strain name | L-Valine (g/L) |
|---|---|---|
| Control | KCCM11201P | 2.7 |
| Test group | M1 | 3.0 |

TABLE 1-continued

| Strain name | L-Valine (g/L) |
|---|---|
| M2 | 2.8 |
| M3 | 2.5 |
| M4 | 4.8 |
| M5 | 3.5 |
| M6 | 3.3 |
| M7 | 2.9 |
| M8 | 3.9 |
| M9 | 3.5 |
| M10 | 2.1 |
| M11 | 1.1 |
| M12 | 2.9 |
| M13 | 2.5 |
| M14 | 3.1 |
| M15 | 4.7 |
| M16 | 3.2 |

Referring to Table 1, M4 and M15 strains, for which the production amounts of valine increased by 178% and 174%, respectively, compared with the KCCM11201P strain as a control, were selected.

EXAMPLE 2

Investigation of Modification Through Gene Sequencing

The main genes in the valine biosynthesis pathway in the M4 and M5 strains with increased valine producing ability were sequenced, and compared with those in the strain KCCM11201P, and the wild-type *Corynebacterium glutamicum* strains ATCC14067, ATCC13032, and ATCC13869. The results identified that the M4 and M15 strains contained the same mutations at specific positions in the promoter region of ilvC, a gene encoding acetohydroxy acid isomeroreductase (AHAIR) (FIG. 1). Specifically, in M4 and M15, the 14th nucleotide G and the 17th nucleotide C were substituted with T in the sequence of the promoter region including the sequence set forth in SEQ ID NO: 5. The sequence set forth in SEQ ID NO: 5 is a sequence that is commonly contained in the promoter region of ilvC of the wild-type *Corynebacterium glutamicum* strains (ATCC14067, ATCC13032, and ATCC13869). In the following examples, it was investigated whether the mutations affected the production amount of an amino acid by the microorganisms of the genus *Corynebacterium*.

EXAMPLE 3

Preparation of Mutation-Introduced Strains and Investigation of Valine Producing Ability

Example 3-1: Preparation of Strains with Introduction of Mutations into *Corynebacterium glutamicum* KCCM11201P and Evaluation of Valine Producing Ability

Example 3-3-1: Preparation of Strains

To substitute the 14th and 17th nucleotides with T in the polynucleotide sequence set forth in SEQ ID NO: 5, a vector containing target mutations for introducing the mutations into the valine-producing strain *Corynebacterium glutamicum* KCCM11201P was constructed.

Specifically, the genomic DNA of ATCC14067, a wild-type *Corynebacterium glutamicum* strain, was extracted by using a G-spin total DNA extraction mini-kit (Intron, Cat.

No. 17045) according to the protocol provided by the kit. PCR was performed using the genomic DNA as a template. To construct a vector for introducing mutations into the promoter region of the ilvC gene, DNA fragments (A and B) were obtained using a primer pair of Primer 1 (SEQ ID NO: 21) and Primer 2 (SEQ ID NO: 22) and a primer pair of Primer 3 (SEQ ID NO: 23) and Primer 4 (SEQ ID NO: 24), respectively.

Overlapping PCR using the two fragments as a template along with Primer 1 (SEQ ID NO: 21) and Primer 4 (SEQ ID NO: 24) was performed to obtain a PCR product of approximately 1.4 kb (hereinafter, referred to as "mutation-introduced fragment"). The primers used are shown in Table 2.

TABLE 2

| Primer | Nucleotide sequence | SEQ ID NO |
|---|---|---|
| Primer 1 | CTATTCTAGAGTGATGAATCTGCAGCAGAAGATC | 21 |
| Primer 2 | GACAACTACATTATTATTATACCACACACATGCA | 22 |
| Primer 3 | TGCATGTGTGTGGTATAATAATAATGTAGTTGTC | 23 |
| Primer 4 | CTATTCTAGAGAAGAGGTCGGTGACGGTCTCAGC | 24 |

The obtained mutation-induced fragments were treated with the restriction enzyme XbaI (New England Biolabs, Beverly, MA), and then ligated using pDZ vector (WO 2008-033001 A1) treated with the same restriction enzyme and T4 ligase (New England Biolabs, Beverly, MA). The prepared gene was transformed into E. coli DH5α, which was then selected from kanamycin-containing LB media, and DNA was obtained using a DNA-spin plasmid DNA purification kit (iNtRON) to thereby construct the recombinant plasmid pDZ-ilvC(Pm3)-14067. The same procedure was performed by using, instead of the genomic DNA of ATCC14067, those of ATCC13869 and ATCC13032, wild-type Corynebacterium glutamicum, and thus the recombinant plasmids named pDZ-ilvC(Pm3)-13869 and pDZ-ilvC(Pm3)-13032 were constructed, respectively.

Among the three recombinant plasmids constructed as above, pDZ-ilvC(Pm3)-14067 was transformed into Corynebacterium glutamicum KCCM11201P, an L-valine-producing strain, by homologous recombination on the chromosome (van der Rest et al., Appl Microbiol Biotechnol 52:541-545, 1999). The strain in which the vector was inserted in the chromosome by recombination of homologous sequences was selected from a medium containing 25 mg/L kanamycin. Thereafter, the transformed strain of Corynebacterium glutamicum for which secondary recombination had been completed was subjected to PCR using Primer 1 and Primer 4 to construct the strain KCCM11201P-ilvC(Pm3) in which mutations were introduced into the ilvC promoter on the chromosome (FIG. 2). The recombinant strain was named Corynebacterium glutamicum CA08-1063, which was internationally deposited at the Korean Culture Center of Microorganisms (KCCM), an international depositary, on 21 Aug. 2019, under the provisions of the Budapest Treaty, and assigned accession number KCCM12574P.

Example 3-1-2: Evaluation of Valine Producing Ability

To compare the valine producing ability between the valine-producing strains Corynebacterium glutamicum KCCM11201P and KCCM11201P-ilvC(Pm3), a fermentation titer evaluation was performed. Each strain was sub-cultured in nutrient media, and then inoculated into a 250 mL corner-baffle flask containing 25 mL of a production medium, and cultured with shaking at 30° C. at 200 rpm for 72 hours. Thereafter, the concentration of L-valine was analyzed using HPLC, and the analyzed concentrations of L-valine were tabulated in Table 3.

<Nutrient Medium (pH 7.2)>
glucose 10 g, meat juice 5 g, polypeptone 10 g, sodium chloride 2.5 g, yeast extract 5 g, agar 20 g, and urea 2 g (based on 1 L of distilled water).
<Production Medium (pH 7.0)>
glucose 100 g, ammonium sulfate 40 g, soy protein 2.5 g, corn steep solids 5 g, urea 3 g, potassium phosphate dibasic 1 g, magnesium sulfate heptahydrate 0.5 g, biotin 100 μg, thiamine-HCl 1 mg, calcium pantothenate 2 mg, nicotine amide 3 mg, calcium carbonate 30 g (based on 1 L of distilled water)

TABLE 3

L-Valine producing ability of KCCM11201P and KCCM11201P-ilvC(Pm3)

| | Strain | L-Valine (g/L) | | | |
|---|---|---|---|---|---|
| | | Batch 1 | Batch 2 | Batch 3 | Mean |
| Control | KCCM11201P | 2.8 | 2.6 | 2.7 | 2.7 |
| Test group | KCCM11201P-ilvC(Pm3) | 3.2 | 2.9 | 2.9 | 3.0 |

As shown in the above results, the L-valine producing ability of the KCCM11201P-ilvC(Pm3) strain was increased by 11% compared with that of the control. Consequently, the L-valine producing ability could be improved through the mutation of the promoter of the ilvC gene.

Example 3-2: Preparation of Strains with Introduction of Mutation into Corynebacterium glutamicum CJ7V and Evaluation of Valine Producing Ability Example 3-2-1: Preparation of Valine-Producing Strain CJ7V To investigate whether the same effect as above was also present in other Corynebacterium glutamicum strains producing L-valine, one species of mutation (ilvN(A42V); Biotechnology and Bioprocess Engineering, June 2014, Volume 19, Issue 3, pp. 456-467) was introduced into the wild-type Corynebacterium glutamicum ATCC14067 to prepare strains having increased L-valine producing ability.

Specifically, the genomic DNA of the strain ATCC14067, a wild-type Corynebacterium glutamicum, was extracted by using a G-spin total DNA extraction mini-kit (Intron, Cat. No. 17045) according to the protocol provided by the kit. PCR was performed using the genomic DNA as a template. To construct a vector for introducing the A42V mutation into the ilvN gene, gene fragments (A and B) were obtained using a primer pair of Primer 5 (SEQ ID NO: 25) and Primer 6 (SEQ ID NO: 26) and a primer pair of Primer 7 (SEQ ID NO: 27) and Primer 8 (SEQ ID NO: 28), respectively. The conditions for PCR were as follows: denaturation at 94° C. for 5 minutes, 25 cycles of denaturation at 94° C. for 30 seconds, annealing at 55° C. for 30 seconds, and polymerization at 72° C. for 60 seconds, and then polymerization at 72° C. for 7 minutes. The primers used are shown in Table 4.

TABLE 4

| Primer | Nucleotide sequence | SEQ ID NO |
|---|---|---|
| Primer 5 | AATTTCTAGAGGCAGACCCTATTCTATGAAGG | 25 |
| Primer 6 | AGTGTTTCGGTCTTTACAGACACGAGGGAC | 26 |
| Primer 7 | GTCCCTCGTGTCTGTAAAGACCGAAACACT | 27 |
| Primer 8 | AATTTCTAGACGTGGGAGTGTCACTCGCTTGG | 28 |

As a result, polynucleotides of 537 bp could be obtained for both of fragments A and B. Overlapping PCR using the two fragments as a template along with Primer 5 (SEQ ID NO: 25) and Primer 8 (SEQ ID NO: 28) was performed to obtain a PCR product of approximately 1044 bp (hereinafter referred to as "mutation-introduced fragment").

The obtained mutation-induced fragments were treated with the restriction enzyme XbaI (New England Biolabs, Beverly, MA), and then ligated using pDZ vector treated with the same restriction enzyme and T4 ligase (New England Biolabs, Beverly, MA). The prepared gene was transformed into *E. coli* DH5α, which was then selected from a kanamycin-containing LB medium, and DNA was obtained using a DNA-spin plasmid DNA purification kit (iNtRON). The vector having a purpose of the introduction of the A42V into the ilvN gene was named pDZ-i/vN (A42V).

Thereafter, the recombinant plasmid pDZ-ilvN(A42V) constructed as above was transformed into wild-type *Corynebacterium glutamicum* ATCC14067 by homologous recombination on the chromosome (van der Rest et al., *Appl Microbiol Biotechnol* 52:541-545, 1999). The strain in which the vector was inserted in the chromosome by recombination of homologous sequences was selected from a medium containing 25 mg/L kanamycin. Thereafter, the transformed strain of *Corynebacterium glutamicum* for which secondary recombination had been completed was subjected to PCR using Primer 5 and Primer 8 to achieve gene fragment amplification, and then the mutation-introduced strain was identified through gene sequencing. The recombinant strain was named *Corynebacterium glutamicum* CJ7V.

Example 3-2-2: Evaluation of Valine Producing Ability

The pDZ-ilvC(Pm3)-14067 was transformed into the *Corynebacterium glutamicum* CJ7V having L-valine producing ability prepared in Example 3-2-1 by way of the same method as in Example 3-1 to thereby prepare a strain with a mutation in the promoter of the ilvC gene, which was named CJ7V-ilvC(Pm3) (FIG. 3). To compare L-valine producing ability between the prepared strains, the strains were cultured and the concentration of L-valine was analyzed by way of the same method as in Example 3-1, and the analyzed concentrations of L-valine were tabulated in Table 5 below.

TABLE 5

L-Valine producing ability of CJ7V and CJ7V-ilvC(Pm3)

| | Strain | L-Valine (g/L) | | | |
|---|---|---|---|---|---|
| | | Batch 1 | Batch 2 | Batch 3 | Mean |
| Control | CJ7V | 3.4 | 3.5 | 3.5 | 3.5 |
| Test group | CJ7V-ilvC(Pm3) | 3.8 | 3.9 | 3.8 | 4.0 |

As shown in the above results, the L-valine producing ability of the CJ7V-ilvC(Pm3) strain was increased by 14% compared with that of the control. That is, it was again identified that the L-valine producing ability could be improved through the mutation of the promoter of the ilvC gene.

Example 3-3: Preparation of Strains with Introduction of Mutation into *Corynebacterium glutamicum* CJ8V and Evaluation of L-Valine Producing Ability Example 3-3-1: Preparation of Valine-Producing Strain CJ8V To investigate whether there was also the same effect as above in other *Corynebacterium glutamicum* strains producing L-valine, one species of mutation (ilvN(A42V)) was introduced into the wild-type *Corynebacterium glutamicum* ATCC13869 to prepare strains having L-valine producing ability by way of the same method as in Example 3-2, and the recombinant strain was named *Corynebacterium glutamicum* CJ8V.

Example 3-3-2: Evaluation of Valine Producing Ability

Strains in which the ilvC promoter mutation was introduced into *Corynebacterium glutamicum* CJ8V having L-valine producing ability prepared in Example 3-3-1 were prepared. Each of the recombinant vectors pDZ-ilvC(Pm3)-14067 and pDZ-ilvC(Pm3)-13869 prepared in Example 3-1-1 was transformed into CJ8V (van der Rest et al., *Appl Microbiol Biotechnol* 52:541-545, 1999). The strain in which the vector was inserted in the chromosome by recombination of homologous sequences was selected on a medium containing 25 mg/L kanamycin. Thereafter, the transformed strain of *Corynebacterium glutamicum* for which secondary recombination had been completed was subjected to PCR using Primer 1 and Primer 4 to construct the strains CJ8V-ilvC(Pm3) and CJ8V-ilvC(Pm3)-2, in which a mutation was introduced into the ilvC promoter on the chromosome (FIG. 4). Of the recombinant strains, CJ8V-ilvC(Pm3)-2 was named *Corynebacterium glutamicum* CA08-2034, which was internationally deposited at the Korean Culture Center of Microorganisms (KCCM), an international depositary, on 21 Aug. 2019, under the provisions of the Budapest Treaty, and assigned accession number KCCM12575P.

To compare L-valine producing ability of the prepared strains, the strains were cultured and the concentration of L-valine was analyzed by way of the same method as in Example 3-1, and the analyzed concentrations of L-valine were tabulated in Table 6 below.

TABLE 6

L-Valine producing ability of CJ8V, CJ8V-ilvC(Pm3), and CJ8V-ilvC(Pm3)-2

| | Strain | L-Valine (g/L) | | | |
|---|---|---|---|---|---|
| | | Batch 1 | Batch 2 | Batch 3 | Mean |
| Control | CJ8V | 3.5 | 3.4 | 3.4 | 3.5 |
| Test group | CJ8V-ilvC(Pm3) | 3.9 | 3.9 | 3.8 | 3.8 |
| Test group | CJ8V-ilvC(Pm3)-2 | 3.8 | 3.8 | 3.8 | 3.8 |

As shown in the above results, the L-valine producing ability of each of the CJ8V-ilvC(Pm3) and CJ8V-ilvC (Pm3)-2 strains was increased by 8.6% compared with that of the control. That is, it was again identified that the L-valine producing ability could be improved through the mutation of the promoter of the ilvC gene.

EXAMPLE 4

Preparation of Isoleucine-Producing Strains and Evaluation of Producing Ability

Example 4-1: Preparation of Strains with ilvC Promoter Mutation Introduced into L-Isoleucine-Producing *Corynebacterium glutamicum* KCCM11248P Strain The strains in which the recombinant plasmids pDZ-ilvC (Pm3)-14067 and pDZ-ilvC(Pm3)-13869 constructed in Example 3-1 were introduced into the L-isoleucine-producing strain, *Corynebacterium glutamicum* KCCM11248P (Korean Patent No. 10-1335789), through homologous recombination on the chromosome, by way of the same method as in Example 3, and these strains were named KCCM11248P::ilvC(Pm3) and KCCM11248P::ilvC(Pm3)-2, respectively (FIG. 5). The prepared strains were cultured by the method as below, and then the isoleucine producing ability was compared.

Each strain was inoculated into a 250 mL corner-baffle flask containing 25 mL of a seed medium, and cultured with shaking at 200 rpm for 20 hours at 30° C. Then, 1 mL of the seed culture was inoculated into a 250 mL corner-baffle flask containing 24 mL of a production medium, and cultured with shaking at 200 rpm for 48 hours at 30° C. The compositions of the seed medium and production medium were as follows.

<Production Medium (pH 7.0)> glucose 20 g, peptone 10 g, yeast extract 5 g, urea 1.5 g, $KH_2PO_4$ 4g, $K_2HPO_4$ 8 g, $MgSO_4$ $7H_2O$ 0.5 g, biotin 100 μg, thiamine HCl 1000 μg, calcium pantothenate 2000 μg, nicotinamide 2000 μg (based on 1 L of distilled water)

<Production Medium (pH 7.0)> glucose 50 g, $(NH_4)_2SO_4$ 12.5 g, soy protein 2.5 g, corn steep solids 5 g, urea 3 g, $KH_2PO_4$ 1 g, $MgSO_4$ $7H_2O$ 0.5 g, biotin 100 μg, thiamine hydrochloride 1000 μg, calcium pantothenate 2000 μg, nicotinamide 3000 μg, $CaCO_3$ 30 g (based on 1 L of distilled water)

Upon the completion of the culture, the L-isoleucine producing ability was measured. The concentrations of L-isoleucine in the culture media for each strain tested are shown in Table 7 below.

TABLE 7

| | | L-Isoleucine (g/L) | | | |
|---|---|---|---|---|---|
| | Strain | Batch 1 | Batch 2 | Batch 3 | Mean |
| Control | KCCM11248P | 1.3 | 1.5 | 1.2 | 1.33 |
| Test group | KCCM11248P-ilvC(Pm3) | 1.8 | 1.5 | 2.0 | 1.76 |
| Test group | KCCM11248P-ilvC(Pm3)-2 | 1.7 | 1.6 | 1.8 | 1.70 |

As shown in Table 7 above, the concentrations of L-isoleucine produced by KCCM11248P::ilvC(Pm3) and KCCM11248::ilvC(Pm3)-2, into which the ilvC promoter enhancement mutation was introduced, were increased by about 32.3% and 27.8%, respectively, compared with that for the L-isoleucine-producing strain KCCM11248P. Therefore, it was identified that L-isoleucine producing ability was improved through the promoter mutation of the ilvC gene. The above results show that the introduction of the ilvC promoter mutation in the L-isoleucine-producing strains of the genus *Corynebacterium* is effective in the production of L-isoleucine.

Example 4-2: Preparation of L-Isoleucine-Producing Strain with ilvC Promoter Mutation Introduced into Wild-Type *Corynebacterium glutamicum* ATCC13032 and Evaluation of L-Isoleucine Producing Ability To investigate the effect of the introduction of the ilvC promoter mutation on L-isoleucine producing ability, strains were prepared by introducing lysC(L377K) variant (KR 10-2019-0003019 A) and hom(G378E) variant (*Appl. Microbiol. Biotechnol.* 45, 612-620 (1996)) into *Corynebacterium glutamicum* ATCC13032 (hereinafter, WT), and ilvA (V383A) mutation (*World J Microbiol Biotechnol* (2015) 31:1369-1377) was introduced into the known gene encoding L-threonine dehydratase, and the L-isoleucine producing ability was compared. The primers used are shown in Table 8.

TABLE 8

| Primer | Nucleotide sequence (5'-3') | SEQ ID NO |
|---|---|---|
| 9 | TCC<u>TCTAGA</u>GCTGCGCAGTGTTGAATACG | 29 |
| 10 | TGGAAATC<u>TTTT</u>CGATGTTCACGTTGACAT | 30 |
| 11 | ACATCGA<u>AAA</u>GATTTCCACCTCTGAGATTC | 31 |
| 12 | GAC<u>TCTAGA</u>GTTCACCTCAGAGACGATTA | 32 |

Example 4-2-1: Introduction of L377K Mutation

PCR was performed using the chromosome of WT as a template along with a pair of Primers 9 and 10 or Primers 11 and 12. The conditions for PCR were: denaturation at 95° C. for 5 minutes, 30 cycles of denaturation at 95° C. for 30 seconds, annealing at 55° C. for 30 seconds, and polymerization at 72° C. for 30 seconds, and then polymerization at 72° C. for 7 minutes. As a result, a 509 bp DNA fragment of the 5'-upstream region of the mutation of the lysC gene and a 520 bp DNA fragment of the 3'-downstream region thereof were obtained, respectively.

PCR was performed using the two amplified DNA fragments as a template along with a pair of Primers 9 and 12. The conditions for PCR were: denaturation at 95° C. for 5 minutes, 30 cycles of denaturation at 95° C. for 30 seconds, annealing at 55° C. for 30 seconds, and polymerization at 72° C. for 60 seconds, and then polymerization at 72° C. for 7 minutes. As a result, a 1011 bp DNA fragment including the mutation of the lysC gene encoding an aspartokinase variant in which the 377th leucine was substituted with lysine was amplified.

The pDZ vector, which cannot be replicated in *Corynebacterium glutamicum,* and the 1011 bp DNA fragment were treated with the restriction enzyme Xbal and ligated using DNA ligase, and then cloned to obtain a plasmid, which was named pDZ-/ysC(L377K).

The pDZ-lysC(L377K) vector obtained as above was introduced into the WT strain by way of an electric pulse method (*Appl. Microbiol. Biotechnol.* (1999), 52:541-545), and then transformed strains were obtained from a selective medium containing 25 mg/L kanamycin. A strain was obtained in which the nucleotide mutation is introduced into the lysC gene by the DNA fragment inserted in the chromosome via a secondary recombinant process (cross-over).

Example 4-2-2: Introduction of G378E Mutation

To construct a vector for the introduction of the hom (G378E) mutation, PCR was performed using the WT genomic DNA as a template along with a pair of Primers 13 and 14 and a pair of Primers 15 and 16. The conditions for PCR were: denaturation at 95° C. for 5 minutes, 30 cycles of denaturation at 95° C. for 30 seconds, annealing at 55° C. for 30 seconds, and polymerization at 72° C. for 30 seconds, and then polymerization at 72° C. for 7 minutes. As a result, a 220 bp DNA fragment of the 5'-upstream region of the mutation of the hom gene and a 220 bp DNA fragment of the 3'-downstream region thereof were obtained, respectively. PCR was performed using the two PCR products as a template along with a pair of Primers 13 and 16. The conditions for PCR were: denaturation at 95° C. for 5 minutes, 30 cycles of denaturation at 95° C. for 30 seconds, annealing at 55° C. for 30 seconds, and polymerization at 72° C. for 30 seconds, and then polymerization at 72° C. for 7 minutes. As a result, a 440 bp DNA fragment including the mutation of hom gene was amplified. The primers used are shown in Table 9.

TABLE 9

| Primer | Nucleotide sequence (5'-3') | SEQ ID NO |
|---|---|---|
| 13 | TCCTCTAGACTGGTCGCCTGATGTTCTAC | 33 |
| 14 | GCCAAAACCTCCACGCGATC | 34 |
| 15 | ATCGCGTGGAGGTTTTGGCT | 35 |
| 16 | GACTCTAGATTAGTCCCTTTCGAGGCGGA | 36 |

The previously used pDZ vector and the 440 bp DNA fragment were treated with the restriction enzyme Xbal, ligated using DNA ligase, and then cloned to obtain a plasmid, which was named pDZ-hom(G378E).

The obtained pDZ-hom(G378E) vector was introduced into the WT::lysC(L377K) strain prepared in Example 4-2-1 by way of an electric pulse method, and then transformed strains were obtained from a selective medium containing 25 mg/L kanamycin. WT::lysC(L377K)-hom(G378E), a strain was obtained in which the nucleotide mutation is introduced into the hom gene by the DNA fragment inserted in the chromosome via a secondary recombinant process (cross-over).

Example 4-2-3: Introduction of ilvC Promoter Mutation

By way of the same methods as in the above examples, strains in which the recombinant plasm ids pDZ-ilvC(Pm3)-14067 and pDZ-ilvC(Pm3)-13032 prepared in Example 3-1 were introduced into the WT::lysC(L377K)-hom(G378E) strain prepared in Example 4-2-2 by homologous recombination on the chromosome, and these strains were named WT::lysC(L377K)-hom(G378E)-ilvC(Pm3) and WT::lysC(L377K)-hom(G378E)-ilvC(Pm3)-3, respectively.

Example 4-2-4: Introduction of ilvA Mutation

To construct a vector in which the previously known livA(V383A) mutation (*World J Microbiol Biotechnol*

(2015) 31:1369-1377) was introduced for the ilvA gene, one pair of primers (Primers 17 and 18) for amplifying the 5'-upstream region of the mutation position and one pair of primers (Primers 19 and 20) for amplifying the 3'-downstream region thereof were designed. The BamHI enzyme site (underlined) was inserted into one end of each of Primers 17 and 20, and a nucleotide substitution mutation (underlined) was positioned at a site designed to crossover in Primers 18 and 19. The primers used are shown in Table 10.

TABLE 10

| Primer | Nucleotide sequence (5'-3') | SEQ ID NO |
|---|---|---|
| 17 | ACGGATCCCAGACTCCAAAGCAAAAGCG | 37 |
| 18 | GCGCTTGAGGTACTCtgcCAGCGTGATGTC | 38 |
| 19 | GACATCACGCTGgcaGAGTACCTCAAGCGC | 39 |
| 20 | ACGGATCCAACCAAACTTGCTCACACTC | 40 |

PCR was performed using the WT chromosome as a template along the pair of Primers 17 and 19 and the pair of Primers 19 and 20. The conditions for PCR were: denaturation at 95° C. for 5 minutes, 30 cycles of denaturation at 95° C. for 30 seconds, annealing at 55° C. for 30 seconds, and polymerization at 72° C. for 30 seconds, and then polymerization at 72° C. for 7 minutes. As a result, a 627 bp DNA fragment of the 5'-upstream region of the mutation of the ilvA gene and a 608 bp DNA fragment of the 3'-downstream region thereof were obtained, respectively. PCR was performed using the two amplified DNA fragments as a template along with a pair of Primers 17 and 20. The conditions for PCR were: denaturation at 95° C. for 5 minutes, 30 cycles of denaturation at 95° C. for 30 seconds, annealing at 55° C. for 30 seconds, and polymerization at 72° C. for 60 seconds, and then polymerization at 72° C. for 7 minutes. As a result, a 1217 bp DNA fragment including the mutation of the ilvA gene encoding an llvA variant in which the 383rd valine was substituted with alanine was amplified.

The pECCG117 (Korean Patent No. 10-0057684) vector and the 1011 bp DNA fragment were treated with the restriction enzyme BamHI, ligated using DNA ligase, and then cloned to obtain a plasmid, which was named pECCG117-ilvA(V383A).

Strains in which the pECCG117-ilvA(V383A) vector was introduced into ATCC13032::hom(G378E)-lysC(L377K)-ilvC(Pm3) and ATCC13032::hom(G378E)-/ysC(L377K)-ilvC(Pm3)-3 were prepared, respectively, and these strains were named ATCC13032::hom(G378E)-lysC(L377K)-ilvC(Pm3)/pECCG117-ilvA(V383A) and ATCC13032::hom(G378E)-lysC(L377K)-ilvC(Pm3)-3/pECCG117-ilvA(V383A), respectively (FIG. 6). In addition, a strain in which only ilvA(V383A) mutation was introduced into ATCC13032::-hom(G378E)-lysC(L377K) was also prepared as a control.

Example 4-2-5: Evaluation of Isoleucine Producing Ability

The strains were cultured by way of the same method shown in Example 4-1, and the concentration of L-isoleucine in the culture was analyzed.

TABLE 11

| | | L-Isoleucine (g/L) | | | |
|---|---|---|---|---|---|
| | Strain | Batch 1 | Batch 2 | Batch 3 | Mean |
| Control | ATCC13032::-hom(G378E)-lysC(L377K)/pECCG117-ilvA(V383A) | 4.1 | 4.3 | 4.3 | 4.23 |
| Test group | ATCC13032::hom(G378E)-lysC(L377K)-ilvC(Pm3)/pECCG117-ilvA(V383A) | 5.2 | 5.1 | 5.6 | 5.30 |
| Test group | ATCC13032::hom(G378E)-lysC(L377K)-ilvC(Pm3)-3/pECCG117-ilvA(V383A) | 5.1 | 5.3 | 5.4 | 5.26 |

As shown in Table 11 above, the concentrations of L-isoleucine in ATCC13032::hom(G378E)-lysC(L377K)-ilvC (Pm3)/pECCG117-ilvA(V383A) and ATCC13032::hom (G378E)-lysC(L377K)-ilvC(Pm3)-3/pECCG117-ilvA (V383A) each including ilvC mutation were increased by about 25% and 24%, respectively, compared with that in the wild-type strain ATCC13032::-hom(G378E)-lysC(L377K)/ pECCG117-ilvA(V383A). The above results show that the introduction of the ilvC promoter mutation in the L-isoleucine-producing strains of the genus *Corynebacterium* is effective in the production of L-isoleucine.

EXAMPLE 5

Preparation of Leucine-Producing Strains and Investigation of Producing Ability

Example 5-1: Preparation of Strain with ilvC Promoter Mutation Introduced into L-Isoleucine-Producing Strains *Corynebacterium glutamicum* KCCM11661P and KCCM11662P and Evaluation of Leucine Producing Ability The pDZ-ilvC(Pm3)-14067 recombinant plasmid constructed in Example 3-1 was transformed into *Corynebacterium glutamicum* KCCM11661P (U.S. Pat. No. 10,351, 859 B2) and KCCM11662P (U.S. Pat. No. 10,351,859 B2), which are L-leucine-producing strains, by homologous recombination on the chromosome (van der Rest et al., *Appl Microbiol Biotechnol* 52:541-545, 1999). The strain in which the vector was inserted in the chromosome by recombination of homologous sequences was selected from a medium containing 25 mg/L kanamycin. Thereafter, the transformed strain of *Corynebacterium glutamicum* for which secondary recombination had been completed was subjected to PCR using Primer 1 and Primer 4 to construct the strains in which a mutation was introduced into the ilvC promoter on the chromosome. The recombinant strains were named *Corynebacterium glutamicum* KCCM 11661 P-ilvC (Pm3) and KCCM11662P-ilvC(Pm3), respectively (FIG. 7). To compare the leucine producing ability between the leucine-producing strains *Corynebacterium glutamicum* KCCM11661P-ilvC(Pm3) and KCCM11662P-ilvC(Pm3), a fermentation titer evaluation was performed. Each strain was subcultured in nutrient media, and then inoculated into a 250 mL corner-baffle flask containing 25 mL of a production medium, and cultured with shaking at 30° C. at 200 rpm for 72 hours. Thereafter, the concentration of L-leucine was analyzed using HPLC, and the analyzed concentrations of L-valine were tabulated in Table 12 below.

<Nutrient Medium (pH 7.2)> glucose 10 g, meat juice 5 g, polypeptone 10 g, sodium chloride 2.5 g, yeast extract 5 g, agar 20 g, and urea 2 g (based on 1 L of distilled water).

<Production Medium (pH 7.0)> glucose 50 g, ammonium sulfate 20 g, corn steep solids 20 g, potassium phosphate dibasic 1 g, magnesium sulfate heptahydrate 0.5 g, biotin 100 μg, thiamine-HCl 1 mg, calcium carbonate 15 g (based on 1 L of distilled water)

TABLE 12

L-Leucine producing ability of KCCM11661P, KCCM11661P-ilvC(Pm3), KCCM11662P, and KCCM11662P-ilvC(Pm3)

| | | L-Leucine (g/L) | | | |
|---|---|---|---|---|---|
| | Strain | Batch 1 | Batch 2 | Batch 3 | Mean |
| Control | KCCM11661P | 2.8 | 2.6 | 2.7 | 2.7 |
| Test group | KCCM11661P-ilvC(Pm3) | 3.1 | 2.9 | 2.9 | 3.0 |
| Control | KCCM11662P | 3.0 | 3.1 | 2.9 | 3.0 |
| Test group | KCCM11662P-ilvC(Pm3) | 3.3 | 3.3 | 3.2 | 3.3 |

As shown in the above results, the L-leucine-producing abilities of the KCCM11661P-ilvC(Pm3) and KCCM11662P-ilvC(Pm3) strains was increased by 11% and 10% compared with that of the control. Therefore, it was identified that the L-leucine producing ability could be improved through the promoter mutation of the ilvC gene.

Example 5-2: Preparation of Strain with Mutation Introduced into Leucine-Producing Strain *Corynebacterium glutamicum* CJL8001 and Evaluation of L-Leucine Producing Ability To investigate whether there was also the same effect as above in other *Corynebacterium glutamicum* strains producing L-leucine, one species of mutation (leuA(R558H, G561D); US 2020-0032305 A1) was introduced into the wild-type strain *Corynebacterium glutamicum* ATCC13032 to prepare strains having improved L-leucine producing ability.

Specifically, the recombinant plasmid pDZ-leuA(R558H, G561D) constructed in the above patent was transformed into wild-type strain *Corynebacterium glutamicum* ATCC130332 by homologous recombination on the chromosome (van der Rest et al., *Appl Microbiol Biotechnol* 52:541-545, 1999). Thereafter, the transformed strain of *Corynebacterium glutamicum* for which secondary recombination had been completed were subjected to gene sequencing to identify the mutation-introduced strain. The recombinant strain was named *Corynebacterium glutamicum* CJL8001.

Last, the pDZ-ilvC(Pm3)-14067 and pDZ-ilvC(Pm3)-13032 vectors were transformed into the *Corynebacterium glutamicum* CJL8001 having L-leucine producing ability by way of the same method as in Example 5-1 to thereby prepare CJL8001-ilvC(Pm3) and CJL8001-ilvC(Pm3)-3, strains in which the mutations were introduced into the ilvC gene (FIG. 8), wherein CJL8001-ilvC(Pm3)-3 was named *Corynebacterium glutamicum* CA13-8101, which was internationally deposited at the Korean Culture Center of Microorganisms (KCCM), an international depositary, on 21 Aug. 2019, under the provisions of the Budapest Treaty, and assigned accession number KCCM12576P.

To compare L-leucine producing ability between the prepared strains, the strains were cultured and the concentration of L-valine was analyzed by way of the same method as in Example 5-1, and the analyzed concentrations of L-leucine were tabulated in Table 13 below.

TABLE 13

| L-Leucine producing ability of CJL8001, CJL8001-ilvC(Pm3), and CJL8001-ilvC(Pm3)-3 | | | | | |
|---|---|---|---|---|---|
| | | L-Leucine (g/L) | | | |
| | Strain | Batch 1 | Batch 2 | Batch 3 | Mean |
| Control | CJL8001 | 3.4 | 3.3 | 3.5 | 3.4 |
| Test group | CJL8001-ilvC(Pm3) | 3.8 | 3.9 | 4.0 | 3.9 |
| Test group | CJL8001-ilvC(Pm3)-3 | 3.9 | 3.9 | 3.9 | 3.9 |

As shown in the above results, the L-leucine producing ability of each of the CJL8001-ilvC(Pm3) and CJL8001- ilvC(Pm3)-3 strains was increased by 15% compared with that of the control. That is, it was again identified that the L-leucine producing ability could be improved through the promoter mutation of the ilvC gene in the microorganism of the genus *Corynebacterium glutamicum*.

From the above description, a person skilled in the art to which the present disclosure pertains will be able to understand that the present disclosure may be embodied in other specific forms without departing from the technical spirit or essential characteristics thereof. Therefore, the embodiments described above should be construed as being exemplified and not limiting the present disclosure. The scope of the present disclosure should be understood such that all changes or modifications derived from the definitions and scopes of the claims and their equivalents fall within the scope of the disclosure.

The invention claimed is:

1. A polynucleotide comprising a nucleotide sequence represented by General Formula 1 below:

X-Y-Z                                              [General Formula 1]

wherein,

X is $CN_1GN_2$,

Y is $CTAATTN_3$, and

Z is CATGTGTGTGGTATAAT, in which $N_1$ of X is cytosine (C) or guanine (G), $N_2$ of X is adenine (A) or thymine (T), and $N_3$ of Y is adenine (A) or guanine (G).

2. The polynucleotide of claim 1, wherein X is any one of SEQ ID NOS: 8 to 11, and Y is SEQ ID NO: 6 or 7.

3. The polynucleotide of claim 1, wherein the polynucleotide comprises any one polynucleotide sequence selected from SEQ ID NOS: 13 to 20.

4. A promoter comprising the polynucleotide of claim 1.

5. A vector comprising the promoter of claim 4 and a gene encoding a target protein.

6. The vector of claim 5, wherein the target protein is acetohydroxy acid isomeroreductase.

7. A microorganism of the genus *Corynebacterium*, comprising the polynucleotide of claim 1.

8. The microorganism of claim 7, wherein the microorganism of the genus *Corynebacterium* is *Corynebacterium glutamicum*.

9. A method for producing a target substance, the method comprising:

culturing the microorganism of the genus *Corynebacterium* of claim 7 in a medium; and recovering the target substance in the medium.

10. The method of claim 9, wherein the target substance is an amino acid.

11. The method of claim 10, wherein the amino acid is an L-branched-chain amino acid.

* * * * *

```
                         SEQUENCE LISTING

<160> NUMBER OF SEQ ID NOS: 40

<210> SEQ ID NO 1
<211> LENGTH: 28
<212> TYPE: DNA
<213> ORGANISM: UNKNOWN
<220> FEATURE:
<223> OTHER INFORMATION: Corynebacterium glutamicum

<400> SEQUENCE: 1
ccgtctaatt gcatgtgtgt ggtagaac                                          28

<210> SEQ ID NO 2
<211> LENGTH: 17
<212> TYPE: DNA
<213> ORGANISM: Artificial Sequence
<220> FEATURE:
<223> OTHER INFORMATION: promoter_general formula Z
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 2
catgtgtgtg gtanaan                                                      17

<210> SEQ ID NO 3
<211> LENGTH: 7
<212> TYPE: DNA
<213> ORGANISM: Artificial Sequence
<220> FEATURE:
<223> OTHER INFORMATION: promoter_general formula Y
<220> FEATURE:
<221> NAME/KEY: misc_feature
<222> LOCATION: (7)..(7)
<223> OTHER INFORMATION: n is a, c, g, or t

<400> SEQUENCE: 3 ctaattn                                                                 7

<210> SEQ ID NO 4
<211> LENGTH: 4
<212> TYPE: DNA
<213> ORGANISM: Artificial Sequence
<220> FEATURE:
<223> OTHER INFORMATION: promoter_general formula X
<220> FEATURE:
```

```
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 4 cngn                                                                      4

<210> SEQ ID NO 5
<211> LENGTH: 17
<212> TYPE: DNA
<213> ORGANISM: Artificial Sequence
<220> FEATURE:
<223> OTHER INFORMATION: promoter_formula Z

<400> SEQUENCE: 5
catgtgtgtg gtagaac                                                        17

<210> SEQ ID NO 6
<211> LENGTH: 7
<212> TYPE: DNA
<213> ORGANISM: Artificial Sequence
<220> FEATURE:
<223> OTHER INFORMATION: promoter_formula Y

<400> SEQUENCE: 6 ctaattg                                                                   7

<210> SEQ ID NO 7
<211> LENGTH: 7
<212> TYPE: DNA
<213> ORGANISM: Artificial Sequence
<220> FEATURE:
<223> OTHER INFORMATION: promoter_formula Y

<400> SEQUENCE: 7 ctaatta                                                                   7

<210> SEQ ID NO 8
<211> LENGTH: 4
<212> TYPE: DNA
<213> ORGANISM: Artificial Sequence
<220> FEATURE:
<223> OTHER INFORMATION: promoter_formula X

<400> SEQUENCE: 8 ccgt                                                                      4

<210> SEQ ID NO 9
<211> LENGTH: 4
<212> TYPE: DNA
<213> ORGANISM: Artificial Sequence
<220> FEATURE:
<223> OTHER INFORMATION: promoter_formula X

<400> SEQUENCE: 9 cgga                                                                      4

<210> SEQ ID NO 10
<211> LENGTH: 4
<212> TYPE: DNA
<213> ORGANISM: Artificial Sequence
<220> FEATURE:
<223> OTHER INFORMATION: promoter_formula X
```

-continued

```
<400> SEQUENCE: 10 cggt                                                                    4

<210> SEQ ID NO 11
<211> LENGTH: 4
<212> TYPE: DNA
<213> ORGANISM: Artificial Sequence
<220> FEATURE:
<223> OTHER INFORMATION: promoter_formula X

<400> SEQUENCE: 11 ccga                                                                    4

<210> SEQ ID NO 12
<211> LENGTH: 17
<212> TYPE: DNA
<213> ORGANISM: Artificial Sequence
<220> FEATURE:
<223> OTHER INFORMATION: promoter_formula Z

<400> SEQUENCE: 12
catgtgtgtg gtataat                                                     17

<210> SEQ ID NO 13
<211> LENGTH: 28
<212> TYPE: DNA
<213> ORGANISM: Artificial Sequence
<220> FEATURE:
<223> OTHER INFORMATION: promoter

<400> SEQUENCE: 13
ccgtctaatt gcatgtgtgt ggtataat                                         28

<210> SEQ ID NO 14
<211> LENGTH: 28
<212> TYPE: DNA
<213> ORGANISM: Artificial Sequence
<220> FEATURE:
<223> OTHER INFORMATION: Promoter

<400> SEQUENCE: 14
ccgtctaatt acatgtgtgt ggtataat                                         28

<210> SEQ ID NO 15
<211> LENGTH: 28
<212> TYPE: DNA
<213> ORGANISM: Artificial Sequence
<220> FEATURE:
<223> OTHER INFORMATION: promoter

<400> SEQUENCE: 15
cggactaatt gcatgtgtgt ggtataat                                         28

<210> SEQ ID NO 16
<211> LENGTH: 28
<212> TYPE: DNA
<213> ORGANISM: Artificial Sequence
<220> FEATURE:
<223> OTHER INFORMATION: promoter

<400> SEQUENCE: 16
cggactaatt acatgtgtgt ggtataat                                         28

<210> SEQ ID NO 17
```

-continued

```
<211> LENGTH: 28
<212> TYPE: DNA
<213> ORGANISM: Artificial Sequence
<220> FEATURE:
<223> OTHER INFORMATION: promoter

<400> SEQUENCE: 17
ccgactaatt gcatgtgtgt ggtataat                                               28

<210> SEQ ID NO 18
<211> LENGTH: 28
<212> TYPE: DNA
<213> ORGANISM: Artificial Sequence
<220> FEATURE:
<223> OTHER INFORMATION: promoter

<400> SEQUENCE: 18
ccgactaatt acatgtgtgt ggtataat                                               28

<210> SEQ ID NO 19
<211> LENGTH: 28
<212> TYPE: DNA
<213> ORGANISM: Artificial Sequence
<220> FEATURE:
<223> OTHER INFORMATION: promoter

<400> SEQUENCE: 19
cggtctaatt gcatgtgtgt ggtataat                                               28

<210> SEQ ID NO 20
<211> LENGTH: 28
<212> TYPE: DNA
<213> ORGANISM: Artificial Sequence
<220> FEATURE:
<223> OTHER INFORMATION: Promoter

<400> SEQUENCE: 20
cggtctaatt acatgtgtgt ggtataat                                               28

<210> SEQ ID NO 21
<211> LENGTH: 34
<212> TYPE: DNA
<213> ORGANISM: Artificial Sequence
<220> FEATURE:
<223> OTHER INFORMATION: primer

<400> SEQUENCE: 21
ctattctaga gtgatgaatc tgcagcagaa gatc                                        34

<210> SEQ ID NO 22
<211> LENGTH: 34
<212> TYPE: DNA
<213> ORGANISM: Artificial Sequence
<220> FEATURE:
<223> OTHER INFORMATION: primer

<400> SEQUENCE: 22
gacaactaca ttattattat accacacaca tgca                                        34

<210> SEQ ID NO 23
<211> LENGTH: 34
<212> TYPE: DNA
<213> ORGANISM: Artificial Sequence
<220> FEATURE:
<223> OTHER INFORMATION: primer

<400> SEQUENCE: 23
```

-continued tgcatgtgtg tggtataata ataatgtagt tgtc                                    34

<210> SEQ ID NO 24
<211> LENGTH: 34
<212> TYPE: DNA
<213> ORGANISM: Artificial Sequence
<220> FEATURE:
<223> OTHER INFORMATION: primer

<400> SEQUENCE: 24
ctattctaga gaagaggtcg gtgacggtct cagc                                    34

<210> SEQ ID NO 25
<211> LENGTH: 32
<212> TYPE: DNA
<213> ORGANISM: Artificial Sequence
<220> FEATURE:
<223> OTHER INFORMATION: primer

<400> SEQUENCE: 25
aatttctaga ggcagaccct attctatgaa gg                                      32

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
agtgtttcgg tctttacaga cacgagggac                                         30

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
gtccctcgtg tctgtaaaga ccgaaacact                                         30

<210> SEQ ID NO 28
<211> LENGTH: 32
<212> TYPE: DNA
<213> ORGANISM: Artificial Sequence
<220> FEATURE:
<223> OTHER INFORMATION: primer

<400> SEQUENCE: 28
aatttctaga cgtgggagtg tcactcgctt gg                                      32

<210> SEQ ID NO 29
<211> LENGTH: 29
<212> TYPE: DNA
<213> ORGANISM: Artificial Sequence
<220> FEATURE:
<223> OTHER INFORMATION: primer

<400> SEQUENCE: 29
tcctctagag ctgcgcagtg ttgaatacg                                          29

<210> SEQ ID NO 30
<211> LENGTH: 30
<212> TYPE: DNA

-continued

```
<213> ORGANISM: Artificial Sequence
<220> FEATURE:
<223> OTHER INFORMATION: primer

<400> SEQUENCE: 30
tggaaatctt ttcgatgttc acgttgacat                                    30

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
acatcgaaaa gatttccacc tctgagattc                                    30

<210> SEQ ID NO 32
<211> LENGTH: 29
<212> TYPE: DNA
<213> ORGANISM: Artificial Sequence
<220> FEATURE:
<223> OTHER INFORMATION: primer

<400> SEQUENCE: 32
gactctagag ttcacctcag agacgatta                                     29

<210> SEQ ID NO 33
<211> LENGTH: 29
<212> TYPE: DNA
<213> ORGANISM: Artificial Sequence
<220> FEATURE:
<223> OTHER INFORMATION: primer

<400> SEQUENCE: 33
tcctctagac tggtcgcctg atgttctac                                     29

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
gccaaaacct ccacgcgatc                                               20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
atcgcgtgga ggttttggct                                               20

<210> SEQ ID NO 36
<211> LENGTH: 29
<212> TYPE: DNA
<213> ORGANISM: Artificial Sequence
<220> FEATURE:
<223> OTHER INFORMATION: primer

<400> SEQUENCE: 36
gactctagat tagtcccttt cgaggcgga                                     29
```

-continued

```
<210> SEQ ID NO 37
<211> LENGTH: 28
<212> TYPE: DNA
<213> ORGANISM: Artificial Sequence
<220> FEATURE:
<223> OTHER INFORMATION: primer

<400> SEQUENCE: 37
acggatccca gactccaaag caaaagcg                                                    28

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38
gcgcttgagg tactctgcca gcgtgatgtc                                                  30

<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39
gacatcacgc tggcagagta cctcaagcgc                                                  30

<210> SEQ ID NO 40
<211> LENGTH: 28
<212> TYPE: DNA
<213> ORGANISM: Artificial Sequence
<220> FEATURE:
<223> OTHER INFORMATION: primer

<400> SEQUENCE: 40
acggatccaa ccaaacttgc tcacactc                                                    28
```